US006346613B1

(12) United States Patent
O'Mahony et al.

(10) Patent No.: US 6,346,613 B1
(45) Date of Patent: Feb. 12, 2002

(54) COMPOSITION AND METHOD FOR ENHANCING PARACELLULAR TRANSPORT ACROSS CELL LAYERS

(75) Inventors: Daniel J. O'Mahony, Dublin (IE); Gerard Cagney, Seattle, WA (US)

(73) Assignee: Elan Corporation, plc, Dublin (IE)

( * ) Notice: Subject to any disclaimer, the term of this patent is extended or adjusted under 35 U.S.C. 154(b) by 0 days.

(21) Appl. No.: 09/160,496

(22) Filed: Sep. 24, 1998

Related U.S. Application Data (60) Provisional application No. 60/059,644, filed on Sep. 24, 1997.

(51) Int. Cl.[7] ............................................. C07H 21/04
(52) U.S. Cl. ..................................................... 536/24.5
(58) Field of Search ........................ 435/6, 91.1, 325, 435/366; 514/44; 536/23.1, 24.31, 24.5

(56) References Cited

U.S. PATENT DOCUMENTS 5,242,906 A 9/1993 Pagano et al. ................. 514/44
5,585,479 A * 12/1996 Hoke et al. ................. 536/24.5

FOREIGN PATENT DOCUMENTS

EP 0 831 148 3/1998

OTHER PUBLICATIONS

Rojanasakul et al., Antisense oligonucleotidde therapeutics: drug delivery and targeting, Advanced Drug Delivery Reviews, vol. 18, pp. 115–131, 1996.*
Gewirtz et al., Facilitating oligonucleotide delivery: helping antisense deliver on its promise, Proc. Natl. Acad. Sci., vol. 93, pp. 3161–3163, Apr. 1996.*
Branch, A good antisense molecule is hard to find, TIBS, vol. 23, pp. 45–50, Feb. 1998.*
Crooke et al., Basic Principles of Antisense Therapeutics, Antisense Research and Application, pp. 1–50, Jul. 7, 1998.*
Hochman and Artursson, "Mechanisms of absorption enhancement and tight junction regulation" *Journal of Controlled Release* 29, 253–267 (1994).

Kevil C. G., et al., "Expression of zonula occludens and adherens juctional proteins in human venous and arterial endothelial cells: role of occludin in endothelial solute barriers" *Microcirculation* 5(2–3) 197–210 (1998).

Ismael J. Hidalgo et al, "Characterization of the Human Colon Carcinoma Cell Line (Caco–2) as a Model Systems for Intestinal Epithelial Permeability" *Gastroenterology* 96:736–49 (1989).

Pierre H. Vachon et al., "Transient Mosaic Patterns of Morphological and Functional Differentiation in the Caco–2 Cell Line" *Gastroenterology* 103:414–423 (1992).

Wong V., et al., "A Synthetic Peptide Corresponding to the Extraacellular Domain of Occludin Perturbs the Tight Junction Permeability Barrier", The Journal of Cell Biology, vol. 136, No. 2, Jan. 27, 1997 399–409.

Furuse M., et al., "Occludin: A Novel Intergral Membrane Protein Localizing at Tight Juctions", The Journal of Cell Biology, vol. 123, No. 6, Part 2, Dec. 1993 1777–1780.

Ando–Akatsuka Y., et al., Interspecies Diversity of the Occluding Sequence: cDNA Cloning of Human, Mouse, Dog, and Rat–Kangaroo Homologues, The Journal of Cell Biology. vol. 133, No. 1, Apr. 1996 43–47.

Furuse, M., et al. "Direct Association of Occludin with ZO–1 and its Possible Involvement in the Localization of Occludin at Tight Junctions", The Journal of Cell Biology, vol. 127, No. 6, Dec. 1994 1617–1626.

* cited by examiner

*Primary Examiner*—Andrew Wang
(74) *Attorney, Agent, or Firm*—Kirsten A. Anderson; Caesar, Rivise, Bernstein, Cohen & Pokotilow, Ltd.

(57) ABSTRACT

A composition and method for enhancing paracellular transport across cell layers in an animal comprising an antisense oligonucleotide hybridizable with a region of the messenger RNA coding for the protein occludin which, when hybridized to the occludin mRNA, interferes with its translation such that occludin function is disrupted and paracellular permeability is increased across an epithelial cell layer or and endothelial cell layer in an animal.

1 Claim, 3 Drawing Sheets

COMPOSITION AND METHOD FOR ENHANCING PARACELLULAR TRANSPORT ACROSS CELL LAYERS

This application claims benefit of Provisional Appln. No. 60/059,644 filed Sep. 24, 1997.

FIELD OF THE INVENTION

The present invention relates to a composition and method for enhancing paracellular transport across cell layers in an animal. More particularly, the present invention provides a composition and method comprising an antisense oligonucleotide hybridizable with a region of messenger RNA coding for the protein occludin (occludin mRNA) which, when hybridized to occludin mRNA, interferes with translation such that occludin function is disrupted and paracellular permeability is increased across an epithelial cell layer or an endothelial cell layer in an animal.

BACKGROUND OF THE INVENTION

Transepithelial and transendothelial transport relate to the movement of solutes across a cell layer. In transcellular transport, solutes move both through and between cells. Movement of solutes through cells, for example across the lumenal and basolateral membranes of epithelial cells, requires transcellular transport. Transcellular transport may be active or passive depending on the solute in question. Active transcellular transport is carrier mediated and energy dependent, and permits solutes to move against their electrochemical gradients. Passive transcellular transport depends on electrochemical gradients generated by active transcellular transport and on the permeability of the cell membrane to the solute.

Movement of solutes between cells, through the tight junctions which bind cells together into a layer as with the epithelial cells of the gastrointestinal tract, is termed paracellular transport. Paracellular transport is passive. Paracellular transport depends on electrochemical gradients generated by transcellular transport and on solvent drag through tight junctions. Tight junctions form an intercellular barrier which separates the apical and basolateral fluid compartments of a cell layer. Movement of a solute through a tight junction from apical to basolateral compartments depends on the "tightness" of the tight junction for that solute.

The "tightness" of tight junctions varies among different epithelial cell layers. For example, in the gastrointestinal tract of the human, tight junctions in the colon are tighter than those in the ileum. In the kidney of the human, tight junctions in the ascending limb of the Loop of Henle are tighter than those in the proximal tubule. The "tightness" of tight junctions also varies among different endothelial cell layers. For example, in the gastrointestinal tract, capillary endothelial cells have irregular tight junctions between adjacent cells enabling passage of some solutes between the cells. In the brain and spinal cord of the human, capillary endothelial cells have virtually continuous tight junctions between the adjacent cells, almost completely preventing passage of solutes between the cells.

Epithelial cell layers and endothelial cell layers present a significant barrier to the movement of solutes across cell layers. This can result in significant problems or barriers for drug absorption regardless of the route of administration of the drug. Therefore, new strategies for delivering drugs across epithelial and endothelial cell layers are needed.

Occludin is a ~65 kD integral membrane protein which is localized at tight junctions in epithelial cell layers and in endothelial cell layers (Furuse et al., J. Cell Biol. 123:1777–1788, 1993). Occludin functions to seal the tight junctions formed between cells in a cell layer. Because occludin is required to maintain the integrity of tight junctions, modulation of occludin synthesis would be desirable to enhance the paracellular permeability of cell layers and, thereby, the movement of solutes, including drugs, across these cell layers.

Thus far, the nucleotide sequences of full length cDNA encoding occludin from human (SEQ ID NO:1), mouse (SEQ ID NO:2), dog (SEQ ID NO:3), chicken (SEQ ID NO:4) (Furuse et al., J. Cell Biol. 123:1777–1788, 1993) and kangaroo rat have been described (Ando-Akatsuka et al., J. Cell Biol. 133:43, 1996). The amino acid sequences of mammalian occludins from human, mouse and dog show approximately 90% homology, whereas the amino acid sequences from mammalian, chicken and rat kangaroo occludins show approximately 50% homology (Ando-Akatsuka et al., J.Cell Biol. 133:43, 1996).

The occludin protein comprises four transmembrane domains, a long carboxyl-terminal cytoplasmic domain, a short amino-terminal cytoplasmic domain, two extracellular loops and one intracellular turn. The nonpolar nature of the extracellular domains and the conservation of their sequences among human, mouse, dog, chicken and kangaroo rat occludin suggest the extracellular domains are important for occludin function.

In view of the location of occludin within tight junctions and the putative structure of occludin, two extracellular loops which face into the tight junction space, transient interference with either occludin synthesis or occludin function may result in a transient increase in paracellular permeability. Such a transient increase in paracellular permeability could enable an increase in drug absorption by paracellular transport across a cell layer with minimal toxic effects.

An antisense oligonucleotide is a sequence of single stranded DNA or RNA synthesized by chemical means in vitro which is "complementary" in sequence to a specific intracellular target DNA or RNA. Antisense oligonucleotides offer the potential to block the expression of specific genes or translation of specific mRNAs within cells. The hydrogen bonding of an antisense oligonucleotide to its complementary mRNA may prevent or block the translation of the mRNA to yield the coded protein by steric hindrance. Alternatively, the interaction between an antisense oligonucleotide and its complementary mRNA within mammalian cells may induce the destruction of that mRNA by RNase H or by other unknown or uncharacterized RNases.

Therefore, what is needed is a composition and method for transiently interfering with occludin mRNA translation so that occludin synthesis and, thereby, occludin function are transiently disrupted and paracellular permeability is transiently enhanced.

SUMMARY OF THE INVENTION

The present invention satisfies the above need by providing a composition and method comprising an oligonucleotide hybridizable with a region of occludin mRNA, or of occludin DNA, which interferes with the translation of the mRNA, or the transcription of the DNA, when hybridized to the mRNA, or the DNA, such that the synthesis of occludin is down-regulated. More specifically, the composition and method of the present invention provides an antisense oligonucleotide which hybridizes with a region of occludin mRNA and, when hybridized to a region of occludin mRNA, interferes with its function such that occludin synthesis is disrupted. This antisense oligonucleotide, when administered in an effective concentration to an animal, including a human, transiently interferes with occludin translation so that occludin function in tight junctions is transiently disrupted, and so that the permeability of the cell layer to solutes, including drugs, is transiently increased.

Therefore, it is an object of the present invention to provide a composition and method for transiently enhancing paracellular transport across a cell layer in an animal including a human.

It is another object of the present invention to provide a composition and method for transiently disrupting the integrity of the tight junctions of an epithelial cell layer in an animal including humans.

It is another object of the present invention to provide a composition and method for decreasing the amount of occludin in the tight junctions of a cell layer.

It is another object of the present invention to provide a composition and method for disrupting the function of occludin in the tight junctions of a cell layer.

It is another object of the present invention to provide a composition and method for transiently disrupting the integrity of the tight junctions of an endothelial cell layer in an animal including a human.

It is another object of the present invention to provide a composition and method for enhancing drug movement across the gastrointestinal epithelium into the systemic circulation of an animal including a human.

It is another object of the present invention to provide a composition and method for enhancing drug movement from the systemic circulation into the interstitial space in an animal including a human.

It is another object of the present invention to provide a composition and method for enhancing drug movement across the pulmonary epithelium into the pulmonary circulation of an animal including a human.

It is another object of the present invention to provide a composition and method for enhancing drug uptake across the blood brain barrier in an animal including a human.

It is another object of the present invention to provide a composition and method for transiently interfering with the translation of occludin mRNA.

It is another object of the present invention to provide a composition and method for transiently interfering with the transcription of the occludin gene.

It is another object of the present invention to provide an antisense oligonucleotide composition that is stable.

It is another object of the present invention to provide an antisense oligonucleotide composition that is able to enter the target cells.

It is another object of the present invention to provide an antisense oligonucleotide composition that is retained by the target cells.

It is another object of the present invention to provide an antisense oligonucleotide composition that is able to interact with its cellular target.

It is another object of the present invention to provide an antisense oligonucleotide composition that interacts specifically with its cellular target.

It is another object of the present invention to provide an antisense oligonucleotide composition that demonstrates low toxicity.

It is another object of the present invention to invention to provide an antisense oligonucleotide composition that can be synthesized easily.

These and other object of the invention will become apparent from a review of the present specification.

DETAILED DESCRIPTION OF THE INVENTION

The present invention relates to antisense oligonucleotide sequences which can hybridize to a region of occludin mRNA or DNA. Such antisense sequences are highly useful for interfering with normal occludin transcription or translation and, thereby, enhancing paracellular transport across cell layers in an animal, including a human.

The antisense oligonucleotides of this invention are complementary to a specific nucleic acid sequence of a region of occludin mRNA. More preferably, the antisense oligonucleotides are complementary to the translation initiation nucleic acid sequence of occludin mRNA. The resultant reduction in occludin protein disrupts tight junctions between the cells in cell layers so that the permeability of the cell layer to solutes, including drugs, is enhanced.

Generally, the oligonucleotide used will have a sequence exactly complementary to a nucleic acid sequence of a region of occludin mRNA. However, absolute complementarity is not required. Any nucleotide having sufficient complementarity to form a stable duplex with a region of occludin mRNA so that hybridization is possible and translation of the RNA is inhibited, for example by duplex formation or RNase H activation, is considered suitable. Stable duplex formation depends on the sequence and length of the oligonucleotide and the degree of complementarity between the antisense oligonucleotide and the target sequence. Therefore, when longer oligonucleotides are used, less complementarity may be required. RNase H activation, on the other hand, may require only 5 contiguous matched base pairs (Monia et al., J. Cell Biol. 268:14514, 1993).

Any oligonucleotide which stably hybridizes to a region of occludin mRNA and which inhibits translation of the mRNA is considered effective. However, the region of occludin mRNA to which the antisense oligonucleotide hybridizes may affect the practice of this invention. That is, oligonucleotides complimentary to specific regions of occludin mRNA including, but not limited to, the translation initiation nucleic acid sequence, the translation elongation nucleic acid sequence and the 3' untranslated region, are particularly effective. Oligonucleotides that inhibit splicing or inhibit 5' capping also may be effective for interfering with translation of occludin mRNA.

The oligonucleotides for use in this invention may be unmodified or modified. Modifications are designed to increase resistance to nuclease attack in vivo, to increase specificity or to increase cellular uptake. Such modifications include, but are not limited to, phosphoramidite modifications (Gryaznon et al., J. Am. Chem. Soc. 116:3143, 1994), phosphorothioate modifications (La Planche et al., Nucleic Acids Res. 14:9081, 1986), methyl phosphanate modifications and short chain alkyl or cycloalkyl modifications. Modifications also may include analogs having one or more modified base forms including purines and pyrimidines not found in nature, oligoribonucleotide analogs including, but not limited to, 2'-methylribonucleotides (Inoue et al., Nucleic Acids Res. 15:6131, 1987), chimeric oligonucleotides (Inoue et al., FEBS Letters 215:327, 1987), O-methyl linkages and other analogs known to those skilled in the art.

Therefore, to enhance the transfection of the occludin antisense oligonucleotide into the cell and into regions of the cell where the occludin mRNA is located, the occludin antisense oligonucleotide may be modified in a variety of ways known to those skilled in the art. However, any such modified oligonucleotide must be functionally interchangeable with the naturally occurring oligonucleotides. That is, it must hybridize effectively with occludin mRNA and interfere with its translation. Alternatively, such modified oligonucleotides may hybridize with the corresponding occludin DNA and interfere with its transcription.

The efficiency of cellular uptake of oligonucleotides may be increased by complexing the oligonucleotides or modified oligonucleotides with a cationic lipid or with a cationic liposome. Cationic lipids include, but are not limited to, lipofectamine, Lipofectin, DOTAP, Transfectam TransfectAce and GS-2888 (Lewis et al., PNAS 93:3177, 1996). The oligonucleotide complexes with the cationic lipid or cationic liposome by ionic interactions and the fusogenic properties of the cationic lipids facilitate cellular uptake of the oligonucleotides. Alternatively, the oligonucleotides may be entrapped in the aqueous space of a liposome (MEV) such as, but not limited to, a cardiolipin:phosphatidylcholine:cholesterol (2:10:7) liposome and then enter the cell by endocytic uptake of the liposome.

Other strategies may include, but are not limited to, conjugating the oligonucleotides with poly (L-lysine) (Leonettie et al., Bioconjug. Chem. 1:149, 1990; Clarenc et al., Anticancer Drug Design, 8:81), polyethylenime (Boussif et al., PNAS, 92:7279, 1995), other "interpolyelectrolyte complexes" (Kabanov et al., Bioconjug. Chem. 6:7, 1995), fusogenic peptides (Plunket et al., J. Biol. Chem. 269:12918, 1995; Bongartz et al., Nucl. Acids Res. 22:4681, 1994) or peptide fragments of the homeodomain of the Drosophila antennaledia protein (Derossi et al., J. Biol. Chem. 269:10444, 1994), transferrin-polylysine conjugates, cholesterol (Ing et al., Nucl. Acids Res. 21:2789, 1993), polyaminilipids including, but not limited to, spermidine-cholesterol or spermine-cholesterol, acridine, peptides and fatty acids. Strategies also include targeting oligonucleotides to cell-surface receptors such as folate (Wang et al., PNAS 92:3318, 1995), asialoglycoprotein receptors (Wu et al., J. Biol. Chem. 267:12436, 1992) and transferrin (Citro et al., PNAS 89:7031, 1992) or to other receptors such as the vitamin $B_{12}$ receptor or the intrinsic factor that associates with the vitamin $B_{12}$ receptor. Targeting of oligonucleotides to specific cells via specific sugar-binding receptors or membrane lectins found on the surface of cells also is contemplated. For example, heme-coated cationic liposomes (Innovir Laboratories, New York) are taken up by liver Kuppfer cells, a small organic structure containing a hydrophobic moiety (INNOPHOR™, Innovir Laboratories, New York) is taken up by all liver cells and poly-lysine-adialoorosomucoid protein conjugates bind to liver-specific AsOR receptors. Further, protein A-bearing neutral liposomes may be used to selectively target cells by incubating them with specific monoclonal antibodies (Mabs).

Occludin antisense oligonucleotides, either alone or after modification or conjugation, may be coupled to the surface of nanoparticles or can be entrapped within nanoparticles or microparticles to enhance their uptake. Examples of nanoparticle carriers include, but are not limited to, cyanoacrylate nanoparticle systems, polylactide systems, polyglycolide systems or polylactide co-glycolide systems, etc.

Once within a cell, the effectiveness of the oligonucleotides can be enhanced by adjuvants that increase endosomal to cytosolic transfer including, but not limited, to fusogenic peptides, 5th generation Starburst dendrimers (Haensler et al., Bioconjug. Chem. 4:372, 1994,), a pH responsive polymer poly(-ethylacrylic acid) (Tirrell et al., Annal. New York Acad. Sci. 446:237, 1985), cationic liposomes and a newly synthesised pH sensitive surfactant N-doclecyl 2-imidazole-propionate or DIP (Hughes et al., Pharmac. Res. 13:404, 1996).

The occludin antisense oligonucleotides of this invention can be administered in a therapeutically effective amount to an animal, including a human, either alone or in combination with a pharmaceutically acceptable carrier. The term "therapeutically effective" means that the amount of occludin antisense oligonucleotide is of sufficient quantity to increase paracellular transport to some beneficial degree. The term "in combination" means that the occludin antisense oligonucleotide and the pharmaceutically acceptable carrier can be administered simultaneously, separately, at different frequencies or by different routes. The term "pharmaceutical combination" includes mixed associations of occludin antisense oligonucleotides and pharmaceutically acceptable carriers and also non-mixed associations such as those found in kits or pharmaceutical packs.

Antisense oligonucleotides, alone or in combination with carriers, can be administered in a single dose or in multiple doses over a period of time. Administration can be oral, parenteral, mucosal, topical, transdermal, by implant, by minipump, by biodegradable polymer matrices, or by any other acceptable route known to those skilled in the art. Administration can be in combination with any biocompatible adjuvant, additive or carrier including, but not limited to, aqueous vehicles and nonaqueous vehicles. Oral administration includes, but is not limited to, tablets, suspensions, solutions, emulsions, capsules, powders, syrups and water compositions. For oral administration, antisense oligonucleotide delivery forms may require some form of enteric coating to prevent their digestion or degradation prior to their absorption in the gastrointestinal tract. In addition, suitable delivery formulation and enteric coatings are contemplated which enable targeted release and sustained delivery in the gastrointestinal tract. Parenteral administration includes, but is not limited to, injection and infusion. Mucosal administration includes, but is not limited to, solutions and sprays. Various additives which enhance the stability, sterility and isotonicity of the composition including, but not limited to, anti microbial preservatives, antioxidants, chelating agents, gelatin and buffers may be added as long as they are compatible with the occludin antisense oligonucleotides.

Dosage range for the administration of the occludin antisense oligonucleotides are those sufficient to produce the desired effect of enhancing paracellular transport. The dosage should not be so large as to cause adverse side effects such as anaphylactic or unwanted cross-reactions or an immune response. Generally, the dosage will vary with the age, condition and sex of the animal, with the physical and chemical properties of the therapeutic agent to be absorbed by paracellular transport, with the cell layer across which the therapeutic agent must be transported, for example the intestinal tract, the lung epithelium, or the blood-brain barrier and with the route of administration. Preferably, dosage of occludin antisense oligonucleotides is above approximately 100 $\mu$M, more preferably above approximately 250 $\mu$M, and most preferably above approximately 500 $\mu$M. However, one skilled in the art can determine the particular therapeutically effective dose of the occludin antisense nucleotide to be used depending upon the circumstances in each case without undue experimentation.

The effect of the occludin antisense oligonucleotides for use in this invention is transient. That is, they interfere with translation of occludin mRNA and enhance paracellular permeability for a limited time. Generally, the amount of time will vary with the physical and chemical properties of the therapeutic agent to be absorbed by paracellular transport. It will also vary with the severity of the disorder to be treated. Preferably, the occludin antisense oligonucleotide will interfere with translation of occludin mRNA so that paracellular permeability is increased from approximately thirty minutes to approximately fourteen days, and more preferably from about one hour to about seven days. However, one skilled in the art can determine the period of time necessary for paracellular absorption of an effective amount of a therapeutic agent without undue experimentation.

The oligonucleotides for use in this invention comprise a sequence of approximately 5 to 100 subunits. More preferably, the oligonucleotides for use in this invention comprise a sequence of approximately 8 to 75 subunits. Most preferably, the oligonucleotides for use in this invention comprise a sequence of approximately 10 to 50 subunits. A "subunit" means a nucleotide base and sugar combination (or a nucleotide analog and/or sugar analog combination) suitably bound to adjacent subunits through phosphodiester or other bonds.

The oligonucleotides of this invention are hybridizable with a region within occludin mRNA and interfere with translation of the mRNA. The functions of mRNA which may be interfered with include, but are not limited to, translocation of the RNA to the site of protein translation, actual translation of the protein from the mRNA decreased stability of the mRNA due to activation of RNases such as RNaseH and possible catalytic activity of the mRNA. Interference with mRNA translation disrupts occludin synthesis and enhances paracellular transport across cell layers in an animal.

Generally, oligonucleotides which hybridize with occludin mRNA or with the parent occludin gene can be used to disrupt occludin synthesis and, thereby, enhance paracellular transport. Triple-helix forming oligonucleotides which hybridize with or interact with sequences within the occludin gene or the promoter which regulates or controls the expression of the occludin gene will also have the desired effect of reducing the amount of occludin mRNA and disrupting occludin synthesis. Preferred are oligonucleotides which hybridize with occludin mRNA. More preferred are oligonucleotides which hybridize with the translation initiation region of occludin mRNA or with those regions of the occludin mRNA which will maximally reduce occludin synthesis, for example, within the coding sequence, the 3' untranslated region, or the 5' untranslated region of the mRNA.

Such oligonucleotides may be useful in diagnostics, therapeutics and as research reagents. For therapeutic use, the oligonucleotide is administered to an animal, including a human, either prior to or at the same time as a therapeutic agent to enhance uptake of the therapeutic agent through paracellular pathways. Any therapeutic agent capable of being administered via epithelial or endothelial cell barriers is encompassed by this invention. Preferably such therapeutic agents include, but are not limited to, autonomic drugs, cardiovascular drugs, pulmonary drugs, gastrointestinal drugs, renal drugs, central nervous system drugs, chemotherapeutic drugs, and dermatologic drugs. More preferably, such therapeutic agents include, but are not limited to, therapeutic agents designed to be absorbed through paracellular pathways.

Therapeutic agents can be administered before, during or after administration of the antisense oligonucleotide. Preferably, therapeutic agents are administered simultaneously with or within 12, 24 or 48 hours following administration of the antisense oligonucleotide.

An alternative approach to decreasing occludin synthesis is to down-regulate the gene coding for occludin mRNA. To do this, a gene which codes for an RNA sequence complementary to the endogenous naturally occurring mRNA coding for occludin (cRNA) is introduced into a cell such as, but not limited to, a jejunal epithelial cell, an ileal epithelial cell, or a capillary endothelial cell. The introduced gene will code for the cRNA sequence which is complementary to the mRNA coding for occludin. Base-pairing of the cRNA with the mRNA within the cell will down-regulate the expression of occludin protein through this cRNA:mRNA interaction.

The gene coding for the cRNA can be introduced into mammalian cells in a viral vector delivery system such as, but not limited to, an adenovirus, an adeno-associated viral vector system, a retrovirus, a herpes simplex virus, or any other gene delivery system known to those skilled in the art.

The gene coding for the cRNA also can be introduced into cells as naked DNA or as naked plasmid molecules containing the gene coding for the cRNA using non-viral means such as, but not limited to, liposomes, lipid-based transmembrane carriers, cytofectins and by encapsulation into polymer systems such as, but not limited to, dendrimer polymer systems, PLGA polymer systems, polycyanoacrylate polymer systems and other polymer systems.

In addition, the gene coding for the cRNA can be associated with chimeric fusion proteins whereby one region of the fusion protein is a DNA binding peptide or protein such as, but not limited to, poly-L-lysine, which binds to the naked DNA or plasmid molecules containing the gene of interest and a second region of the chimeric fusion protein bind to and targets chosen receptor sites in, for example, the epithelial cells of the gastrointestinal tract such as, but not limited to, the vitamin $B_{12}$ transporter, the glucose transporter, the HPT-1 receptor, the PEPT1 transporter, the D2H protein, the human sucrase-isomaltase complex, the folate receptor or any other receptor expressed on the apical membrane of epithelial cells. Likewise, the second region of the chimeric fusion protein can bind to and target chosen receptor sites expressed on the apical membrane of endothelial cells.

Furthermore, the chimeric fusion protein may contain a third region termed a Nuclear Localization Signal or Nuclear Localization Sequence (NLS) which will traffic the complex of the chimeric fusion protein associated with the gene/DNA/plasmid molecule of interest to the nucleus of the cell once this complex has traversed the plasma membrane and entered the cytoplasm of the cell.

Synthetic peptides of both linear and cyclic conformation corresponding to extracellular loop domains of occludin also may be used to interfere with occludin function in the tight junctions of cell layers and, thereby, to increase paracellular transport of therapeutic agents across a cell layer.

The following examples will serve to further illustrate the present invention without, at the same time, constituting any limitation on the present invention. On the contrary, it is to be clearly understood that resort may be had to various other embodiments, modifications and equivalents thereof which, after reading the description herein, may suggest themselves to those skilled in the art without departing from the spirit of the present invention and/or the scope of appended claims.

EXAMPLE 1
Culture of Caco-2 Cells

Human intestinal Caco-2 cells were grown using standard techniques well known to those skilled in the art. The cells were seeded onto polycarbonate filters (Costar Snapwells; diameter=12 mm; area=1.13 $cm^2$; pore size=0.4m) at a density of $0.5 \times 10^6$ $cm^2$. For antisense oligonucleotide studies, 18–25 day old cell monolayers were used which have transepithelial electrical resistance (TER) measurements in the range 200–400 $cm^{2\cdot}$

EXAMPLE 2
Antisense Oligonucleotide Treatment

All incubations were at 37° C. in 5% $CO_2$ atmosphere. All solutions were warmed to 37° C. before use. The following procedure was carried out once a day over three days. After reading the TER, the cells were washed once and incubated in a reduced serum medium (RSM; Opti-MEM 1 with GlutaMax 1; Gibco-BRL) for 30 minutes. Meanwhile, the lipofectamine-oligonucleotide complex was allowed to form at room temperature. Lipofectamine (20 μl/snapwell; Gibco BRL CN. 18324-012) was mixed with occludin antisense DNA oligonucleotide, with occludin scrambled oligonucleotide or with water control in RSM. Antisense oligonucleotides (phosphorothioate oligonucleotides) synthesized by Genosys (Cambridge, UK) were designed to hybridize with the translation initiation region of human occludin mRNA, as follows: Occludin antisense oligonucleotide used is:

5' AAG AGG CCT GGA TGA CA 3'    (SEQ ID NO:5)

Occludin scrambled oligonucleotide used is:

5' GCA AGT CAG GAC GTA GA 3'    (SEQ ID NO:6)

The lipofectin:oligonucleotide complex was added to the apical surface of the snapwells and the cells were incubated for 2 hours. The apical and basolateral media were then replaced with normal medium (except on day 4). After the 2 hour incubation on day 3, transepithelial flux of $^3$H-mannitol was measured.

EXAMPLE 3
$^3$H-mannitol Flux

Caco-2 cells were washed once in buffered Hank's balanced salt solution (bHBSS; Gibco CN.14065-031; supplemented with 0.011M glucose, 15 mM HEPES acid [3.575 g/l; Sigma CN.H3375], 10 mM HEPES base [2.603 g/l; Sigma CN. H1016]) and were incubated 30 minutes. The apical reservoir bHBSS was replaced with 1 ml buffered HBSS containing 1 μCi/ml of the hydrophilic marker $^3$H-mannitol (New England Biolabs). A 10 μl sample of the stock solution was retained for later measurement and 10 μl apical samples were taken at the end of the experiment. One ml samples from the basolateral reservoirs were taken at appropriate time points (90 minutes or 120 minutes post addition of $^3$H-mannitol). After each basolateral sampling, the snapwells were placed in fresh 6-well plates and 2 ml of prewarmed bHBSS was added to the basolateral reservoir. The samples were added to 4 ml scintillation fluid and radioactivity for each vial counted on a scintillation counter.

EXAMPLE 4
Treatment of Cultured Human Epithelial Cells With Occludin Antisense Oligonucleotide.

Fully differentiated Caco-2 monolayers were grown as in Example 1 and were subjected to antisense treatment as in Example 2.

Table 1 shows the number of passages and the age of the cells used in the studies detailed in Experiment 1 in Example 5 and Experiment 2 in Example 6.

TABLE 1

|  | Passage | Age of Cells |
| --- | --- | --- |
| Experiment 1 | 32 | 16 |
| Experiment 2 | 42 | 28 |

EXAMPLE 5
Effect of Occludin Antisense Treatment on Mannitol Flux Across Caco-2 Cells Fully differentiated Caco-2 monolayers were grown as in Example 1. The cells were treated over 3 days with lipofectamine alone, lipofectamine and occludin antisense oligonucleotide (Sequence ID No.5) or lipofectamine and occludin scrambled oligonucleotide, (Sequence ID No.6) at 5 μM on day 1, 50 μM on day 2 and 500 μM on day 3 as in Example 2. On day 4, [$^3$H]-mannitol was applied to the apical domain and flux was determined by measuring the radioactivity (cpm) transferred to the basolateral reservoir over 90 minutes as in Example 3.

Figure 1:
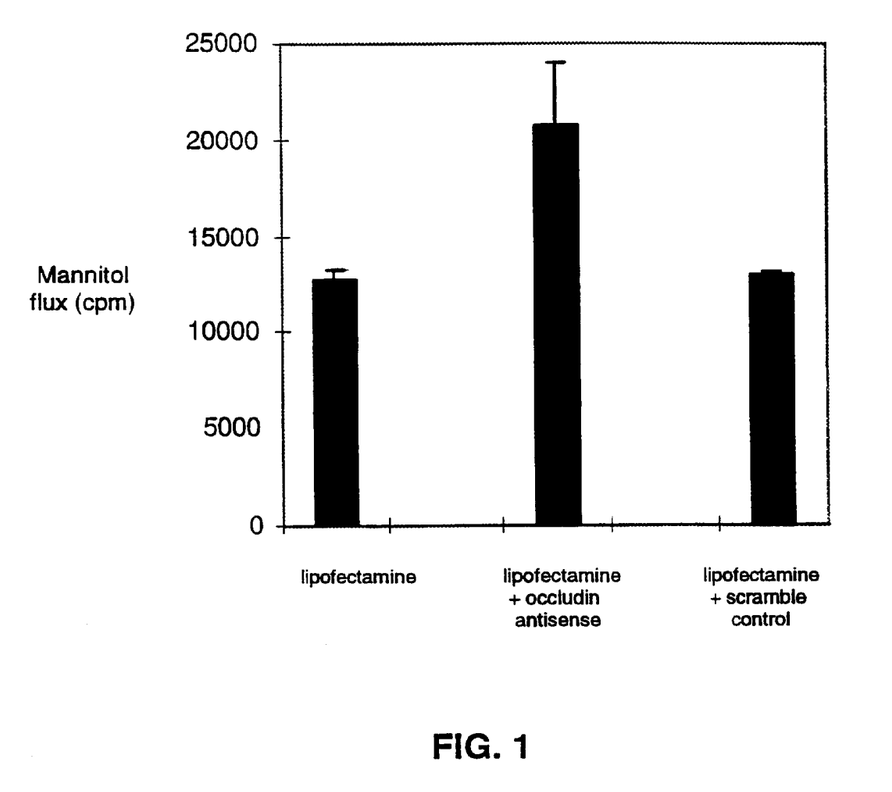
FIG. 1 shows the effect of occludin antisense oligonucleotide treatment on the flux of the hydrophilic marker [$^3$H]-mannitol across polarized Caco-2 monolayers after 90 minutes.

Table 2 and FIG. 1 show the effect of lipofectamine alone of lipofectamine+occludin antisense oligonucleotide (SEQ ID NO:5) and of lipofectamine+occludin scrambled oligonucleotide (SEQ ID NO: 6) on [$^3$H]-mannitol flux in polarized Caco-2 cells measured after 90 minutes as in Example 3.

TABLE 2

[$^3$H]-mannitol flux in polarized Caco-2 cells.

| Treatment | Snapwells | TER | (cpm/ml) | Mean | S.D |
| --- | --- | --- | --- | --- | --- |
| Lipofectamine | 1 | 1050 | 12955 | | |
| | | | 13340 | | |
| | 2 | 1220 | 12290 | | |
| | | | 12300 | | |
| | | | | 12721 | 3385.7 |
| Lipofectamine + Occludin Antisense | 3 | 1260 | 19463 | | |
| | | | 26644 | | |
| | 4 | 1410 | 17550 | | |
| | | | 19310 | | |
| | | | | 20742 | 6402.5 |
| Lipofectamine + Scrambled Antisense | 5 | 1280 | 12898 | | |
| | | | 13015 | | |
| | 6 | 1700 | 14075 | | |
| | | | 12094 | | |
| | | | | 13020 | 2527.5 |
| Apical Reservoir (pooled) | | | 4845771 | | |
| | | | 4943129 | | |

FIG. 1 shows the effect of lipofectamine alone of lipofectamine+occludin antisense (SEQ ID NO:5) and of lipofectamine+occludin scrambled (SEQ ID NO:6) on [$^3$H]-mannitol flux in polarized Caco-2 cells measured after 90 minutes as in Example 3.

The data in Table 2 and in FIG. 1 demonstrate that treatment of Caco-2 cells with occludin antisense oligonucleotide lead to a 1.6 fold increase in flux relative to no oligonucleotide and to a 1.6 fold increase in flux relative to occludin scrambled oligonucleotide.

EXAMPLE 6
Effect of Occludin Antisense Treatment on Mannitol Flux Cross Caco-2 Cells Lipofectamine (20 μl/snapwell; Gibco BRL CN. 18324-012) was mixed with 500 μM of occludin antisense (SEQ ID NO:5) or of water control in RSM and was added to the cells as in Example 2.

The synthetic phosphorothioate oligonucleotides were complementary to the translation initiation region of human occludin mRNA (SEQ ID NO:5) and were designed to inhibit translation of the occludin protein. A negative control oligonucleotide, occludin scrambled (SEQ ID NO:6) was also used.

Table 3 shows the effect of lipofectamine (Lip), of lipofectamine+occludin scrambled (Occ Neg), of lipofectamine+occludin antisense (Occ Pos) and of water (No Treatment) on [$^3$H]-mannitol flux in polarized Caco-2 cells measured after 90 minutes as in Example 3.

TABLE 3

$^3$H mannitol flux in polarized Caco-2 cells

|   | Lip | Occ Neg | Occ Pos | No Treatment |
|---|---|---|---|---|
| 1 | 1743 | 1789 | 2058 | 1629 |
| 2 | 1964 | 1948 | 4245 | 1657 |
| 3 | 2547 | 1815 | 4266 | 1822 |
| 4 | 2963 | 1666 | 4918 | 2654 |
| 5 | 1861 | 1738 | 4662 | 2065 |
| 6 | 3743 | 2498 | 5135 | 1122 |
| av | 2470.167 | 1909 | 4214 | 1824.833 |
| sd | 777.8114 | 303.3045 | 1113.244 | 511.0184 |

Figure 2:
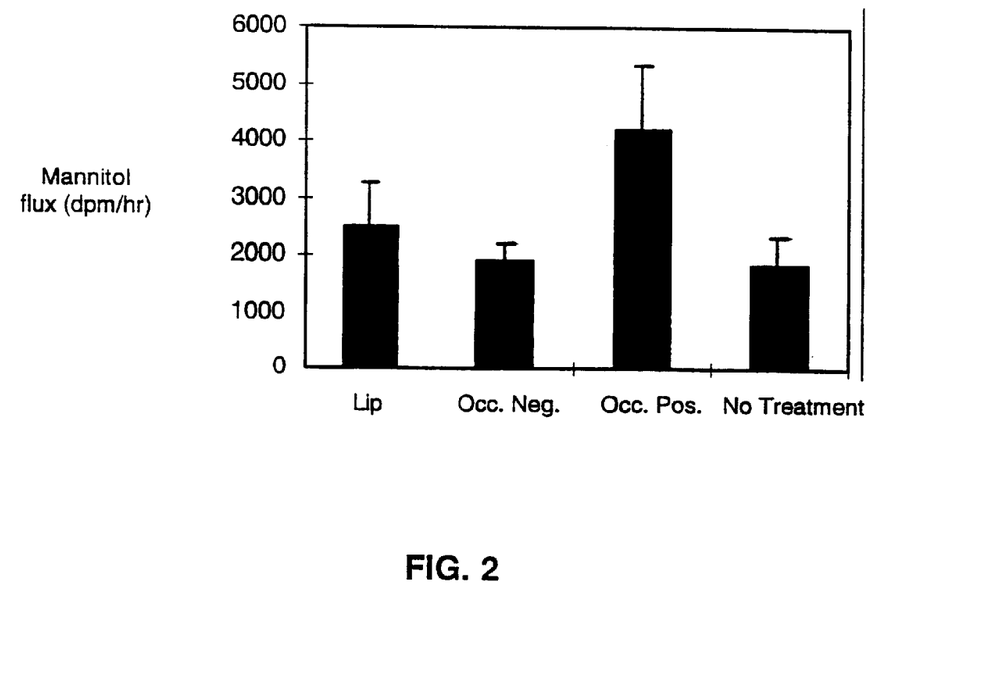
FIG. 2. shows the effect of occludin antisense oligonucleotide treatment on flux of the hydrophilic marker [$^3$H]-mannitol across polarized Caco-2 after 180 minutes.

FIG. 2 shows the effect of lipofectamine, of lipofectamine+occludin scrambled (SEQ ID NO:6), of lipofectamine+occludin antisense (SEQ ID NO:5) and of water on the flux of the [$^3$H]-mannitol in Caco-2 monolayers grown on snapwells as in Example 2. In this experiment, antisense treatment led to a mean 2.2-fold increase in [$^3$H]-mannitol flux relative to control scrambled sequence antisense DNA. The cells were treated over 3 days with lipofectamine alone, lipofectamine+occludin scrambled, lipofectamine+occludin antisense and water. On day 4, [$^3$H]-mannitol was applied to the apical domain and the fluxes were determined by measuring the radioactivity (dpm) transferred to the basolateral reservoir over 120 minutes as in Example 3.

Figure 3:
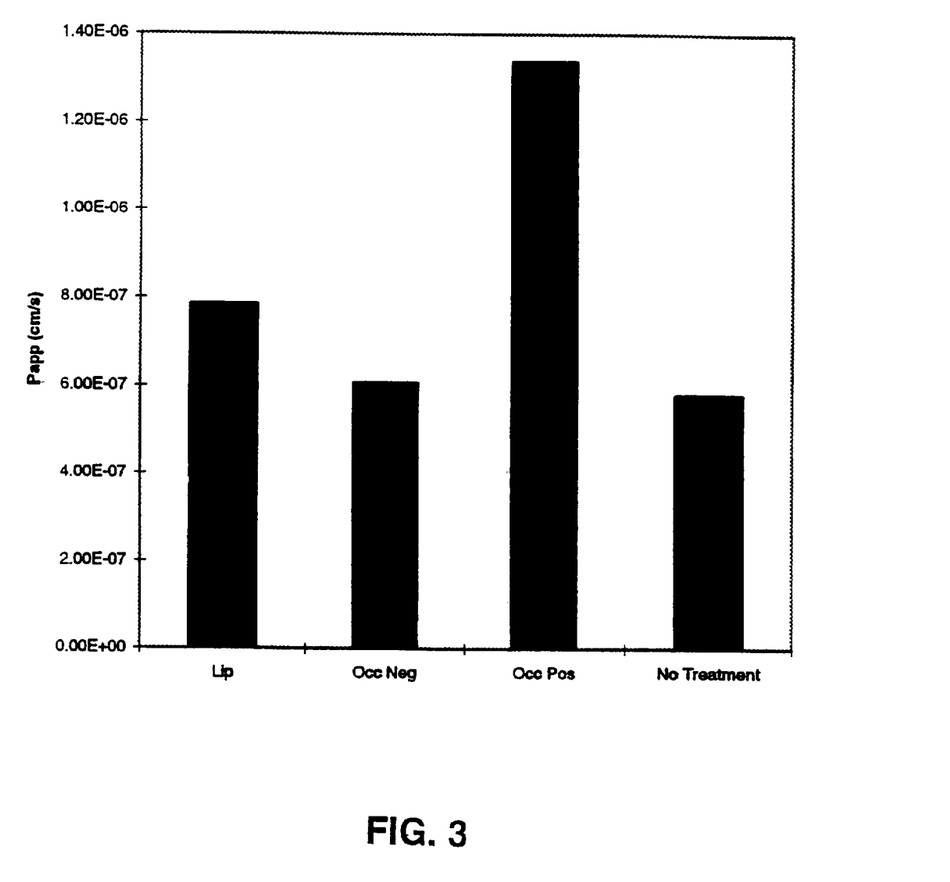
FIG. 3 shows the effect of occludin antisense oligonucleotide treatment on the apparent permeability of Caco-2 monolayers to the hydrophilic marker mannitol.

FIG. 3 shows the apparent permeability values (Papp) of the polarized Caco-2 cells to [$^3$H]-mannitol. The cells were treated with lipofectamine, lipofectamine+500 μM occludin scrambled (SEQ ID NO:6), lipofectamine+500 μM occludin antisense (SEQ ID NO:5) or water. Apparent permeability values (Papp) were calculated according to the equation $$P\text{app} = (dQ/dt)(1/C.A)$$

where $dQ/dt$ = flux rate (mmol/s)

$C$ = concentration on donor side at $t = 0$ mmol/cm$^3$)

$A$ = area of monolayer (cm$^2$).

The apparent permeability of the monolayers was 415.78 cm s$^{-1}$ for cells treated with the specific occludin antisense DNA compared to 188.35 cm s$^{-1}$ for cells treated with a scrambled control oligonucleotide. This difference is statistically significant ($p=0.0045$; 2-tailed unpaired t test). These data demonstrate that an antisense oligonucleotide targeted to human occludin mRNA mediates increased paracellular permeability from apical to basolateral compartments in cultured human intestinal epithelial cells.

It will be apparent to one of ordinary skill in the art that various changes and modifications can be made without departing from the spirit and scope of the invention. The references mentioned herein are all hereby incorporated by reference in their entireties.

We claim:

1. An antisense oligonucleotide having a sequence hybridizable with a region of occludin mRNA such that the translation of occludin is disrupted, wherein the nucleotide sequence of the oligonucleotide is Seq. ID No: 5.

* * * * *

SEQUENCE LISTING

```
<160> NUMBER OF SEQ ID NOS: 6

<210> SEQ ID NO 1
<211> LENGTH: 2377
<212> TYPE: DNA
<213> ORGANISM: Homo sapiens
<300> PUBLICATION INFORMATION:
<302> TITLE: Interspecies Diversity of the Occludin Sequence: cDNA
      Cloning of Human, Mouse, Dog, and Rat-Kangaroo Homologues
<303> JOURNAL: J. Cell Biol.
<304> VOLUME: 133
<305> ISSUE: 1
<306> PAGES: 43-47
<307> DATE: April 1996
<308> DATABASE ACCESSION NUMBER: U41984, U49221, U41985

<400> SEQUENCE: 1
ctcccgcgtc cacctctccc tccctgcttc ctctggcgga ggcggcagga accgagagag      60
gtccagagcg ccgaggagcc ggtctaggac gcagcagatt ggtttatctt ggaagctaaa     120
gggcattgct catcctgaag atcagctgac cattgacaat cagccatgtc atccaggcct     180
cttgaaagtc cacctcctta caggcctgat gaattcaaac cgaatcatta tgcaccaagc     240
aatgacatat atggtggaga gatgcatgtt cgaccaatgc tctctcagcc agcctactct     300
ttttacccag aagatgaaat tcttcacttc tacaaatgga cctctcctcc aggagtgatt     360
```

```
cggatcctgt ctatgctcat tattgtgatg tgcattgcca tctttgcctg tgtggcctcc      420
acgcttgcct gggacagagg ctatggaact tccctttttag gaggtagtgt aggctaccct     480
tatggaggaa gtggctttgg tagctacgga agtggctatg ctatggcta tggttatggc      540 tatggctacg gaggctatac agacccaaga gcagcaaagg gcttcatgtt ggccatggct     600 gcctttttgtt tcattgccgc gttggtgatc tttgttacca gtgttataag atctgaaatg    660
tccagaacaa gaagatacta cttaagtgtg ataatagtga gtgctatcct gggcatcatg    720
gtgtttattg ccacaattgt ctatataatg ggagtgaacc caactgctca gtcttctgga    780
tctctatatg gttcacaaat atatgccctc tgcaaccaat tttatacacc tgcagctact    840
ggactctacg tggatcagta tttgtatcac tactgtgttg tggatcccca ggaggccatt    900
gccattgtac tggggttcat gattattgtg gcttttgctt taataatttt ctttgctgtg    960
aaaactcgaa gaaagatgga caggtatgac aagtccaata ttttgtggga caaggaacac    1020
atttatgatg agcagccccc caatgtcgag gagtgggtta aaaatgtgtc tgcaggcaca    1080
caggacgtgc cttcaccccc atctgactat gtggaaagag ttgacagtcc catggcatac    1140
tcttccaatg gcaaagtgaa tgacaagcgg ttttatccag agtcttccta taaatccacg    1200
ccggttcctg aagtggttca ggagcttcca ttaacttcgc ctgtggatga cttcaggcag    1260
cctcgttaca gcagcggtgg taactttgag acaccttcaa aaagagcacc tgcaaaggga    1320
agagcaggaa ggtcaaagag aacagagcaa gatcactatg agacagacta cacaactggc    1380
ggcgagtcct gtgatgagct ggaggaggac tggatcaggg aatatccacc tatcacttca    1440
gatcaacaaa gacaactgta caagaggaat tttgacactg gcctacagga atacaagagc    1500
ttacaatcag aacttgatga gatcaataaa gaactctccc gtttggataa agaattggat    1560
gactatagag aagaaagtga agagtacatg gctgctgctg atgaatacaa tagactgaag    1620
caagtgaagg gatctgcaga ttacaaaagt aagaagaatc attgcaagca gttaaagagc    1680
aaattgtcac acatcaagaa gatggttgga gactatgata gacagaaaac atagaaggct    1740
gatgccaagt gtttgagaa attaagtatc tgacatctct gcaatcttct cagaaggcaa    1800
atgactttgg accataaccc cggaagccaa acctctgtga gcatcacaaa gttttggttg    1860
ctttaacatc atcagtattg aagcatttta taaatcgctt ttgataatca actgggctga    1920
acactccaat taaggatttt atgctttaaa cattggttct tgtattaaga atgaaatact    1980
gtttgaggtt tttaagcctt aaaggaaggt tctggtgtga actaaacttt cacaccccag    2040
acgatgtctt catacctaca tgtatttgtt tgcataggtg atctcattta atcctctcaa    2100
ccacctttca gataactgtt atttataatc acttttttcc acataaggaa actgggttcc    2160
tgcaatgaag tctctgaagt gaaactgctt gtttcctagc acacactttt ggttaagtct    2220 gtttatgac ttcattaata ataaattccc tggcctttca tattttagct actatatatg     2280
tgatgatcta ccagcctccc tattttttt ctgttatata aatggttaaa agaggttttt     2340
cttaaataat aaagatcatg taaaagtaaa aaaaaaa                              2377
```

<210> SEQ ID NO 2
<211> LENGTH: 1961
<212> TYPE: DNA
<213> ORGANISM: Canis familiaris
<300> PUBLICATION INFORMATION:
<302> TITLE: Interspecies Diversity of the Occludin Sequence: cDNA
      Cloning of Human, Mouse, Dog, and Rat-Kangaroo Homologues
<303> JOURNAL: J. Cell Biol.
<304> VOLUME: 133
<305> ISSUE: 1

<306> PAGES: 43-47
<307> DATE: April 1996
<308> DATABASE ACCESSION NUMBER: U41984, U49221, U41985

<400> SEQUENCE: 2

```
caggttggct tattttgggg agctctggga tcctgctcgt cctgaagatc gggtgatcat      60
tgacatcagc catgtcatcg aggccttttg agagtccacc tccgtataga cctgatgaat     120
tcaaacccaa tcattatgca ccgagcaatg atgtgtacgg tggggacatg cacgtccgac     180
ccatgctctc tcagccggcg tattctttct acccagaaga tgaaattctt cacttctaca     240
aatggacctc tcctccagga gtaattcgga ttctgtccat gcttgtcatt gtgatgtgca     300
tcgccatatt tggctgtgtc gcgtccacgc tcgcctggga tagaggctat ggaactggct     360
taatgggtgg tagcataggc taccettacg aagtggctt cgggagctac gggactggct      420
acggctacgg gtttggctac ggctacggct acggcggcta cacggatccc agagcagcaa     480
agggcttcct cctggccatg gtggcctttt gttttatcgc tgcattggtg atatttgtta     540
ccagcgttat aaggtctgac atatccgaaa ccagaaggta ctacttgact gtaataatac     600
tgagtgcctt cctgggcgtc atgatgttca ttgctacaat tgtctatata atgggagtca     660
atccaactgc ccaggcttct gggtctttat acagttcaca gatatatgcc atgtgcaacc     720
agttctatgc atctacagct accggactct acatggatca gtatttgtat cactactgtg     780
tggtggatcc ccaagaggca attgccattg tcctgggatt catggtgatt gtggcttttg     840
ctttaataat tttctttgct gtgaaaactc gaagaaagat ggaccggtat gacaagtcga     900
atatattgtg ggacaaggaa catatttatg atgaacaacc ccccaatgtt gaagagtggg     960
ttaaaaacgt ttctgcaggc acacaagaca tgcctcctcc cccttctgac tatgtggaga    1020
gagtggacag tcccatggcg tactcttcca atggtaaagt gaatgacaag cggttgtatc    1080
cagagtcttc ctataaatca acaccggtcc ccgaagtggt gcaggagctg cccgccacct    1140
cccctgcgga tgacttcagg cagcctcgct acagcagcag cgggcacttg agccaccctt    1200
cgaagagggc cccctcgaaa ggaagaacgg gaaggcccaa gaggctggag caggaccact    1260
atgagacaga ctacacgacg ggcggcgagt cgtgtgacga gctggaggag gactggatca    1320
gggaatatcc acctatcact tcagatcaac aaagacaact ctacaagaga aattttgaca    1380
ctggcctgca ggaatacaag agcttacaag cagaacttga tgagatcaat aaagaactct    1440
ctcgcctgga taaagaattg gatgactata gagaagaaag tgaagagtac atggctgctg    1500
ctgatgagta caatagactg aagcaagtta agggatctcc agattacaaa ataagagga     1560
attattgcaa gcagttgaag agcaaattgt cccacatcaa gaagatggtt ggagactatg    1620
atagacagaa aacatagaag gcagatgcca cacagtttga gagattgtga agtatttgac    1680
atatctgcaa cgttgtcaga aggcagaatg actttggatt tcgaacccag gaggccagat    1740
ctttgtgatc attacaaagt tttggtagct ttaatatcat cagtattgaa gcattttaca    1800
catagctttt gataatcaac tgggctgaac actcccgatt aaggattctg tgctttagac    1860
tttggctgtt gtgctaaagg actgagtata ggtggaggtt ttcagacctt ggaagaaggt    1920
cccacggtga acttgtgctg tgaacttgca cacttggggc a                       1961
```

<210> SEQ ID NO 3
<211> LENGTH: 2839
<212> TYPE: DNA
<213> ORGANISM: Mus musculus
<300> PUBLICATION INFORMATION:
<302> TITLE: Interspecies Diversity of the Occludin Sequence: cDNA Cloning of Human, Mouse, Dog, and Rat-Kangaroo Homologues
<303> JOURNAL: J. Cell Biol.
<304> VOLUME: 133
<305> ISSUE: 1
<306> PAGES: 43-47
<307> DATE: April 1996
<308> DATABASE ACCESSION NUMBER: U41984, U49221, U41985

<400> SEQUENCE: 3

| | | | | | |
|---|---|---|---|---|---|
| ggagtttcag | gtgaatgggt | caccgaggga | ggaggctggc | cacgccacac | ctcgtcgcta | 60 |
| gtgcccacct | cccggcccct | ctttccttag | gcgacagcgg | tggagttgcg | ggagagcggt | 120 |
| ccagcgcacg | gagcaaccgg | ctaggggctc | ggcaggttcg | cttatcttgg | gagcctggac | 180 |
| attttgctca | tcataaagat | taggtgacca | gtgacatcag | ccatgtccgt | gaggcctttt | 240 |
| gaaagtccac | ctccttacag | acctgatgaa | ttcaaaccca | atcattatgc | accaagcaat | 300 |
| gacatgtatg | gcggagagat | gcatgtccgg | ccgatgctct | ctcagccagc | gtactctttt | 360 |
| tatccggaag | atgaaattct | tcacttctac | aaatggacgt | cgcccccagg | ggtgatccgg | 420 |
| atcctgtcta | tgctcattat | tgtgatgtgc | atcgccatat | ttgcctgtgt | ggcttccaca | 480 |
| cttgcttggg | acagaggcta | tgggacaggg | ctctttggag | gaagcctaaa | ctacccttat | 540 |
| agtggctttg | gctacggagg | tggctatgga | ggcggctatg | gaggctatgg | ctatggctat | 600 |
| ggcggatata | cagacccaag | agcagccaaa | ggcttcctgt | tggccatggc | agccttctgc | 660 |
| ttcatcgctt | ccttagtaat | atttgtgacc | agtgttataa | gatctggaat | gtccaggaca | 720 |
| agaagatatt | acttgatcgt | gatcatagtc | agcgctatcc | tggcatcat | ggtgtttatt | 780 |
| gccacgatcg | tgtacataat | gggagtgaac | ccgacggccc | aggcttctgg | atctatgtac | 840 |
| ggctcacaga | tatatatgat | ctgcaaccag | ttttatactc | ctggaggtac | tggtctctac | 900 |
| gtggatcaat | atttgtatca | ctactgtgtg | ttgatcccc | aggaggctat | agccattgtc | 960 |
| ctggggttca | tgattatcgt | ggcttttgct | ttaatcatct | tttttgctgt | gaaacccga | 1020 |
| agaaagatgg | atcggtatga | taagtccaat | attttgtggg | ataaggaaca | catttatgat | 1080 |
| gaacagcccc | ccaatgttga | agagtggggtt | aaaaatgtgt | ctgcaggcac | acaggacatg | 1140 |
| cctccacccc | catctgacta | tgcggaaaga | gttgacagtc | caatggccta | ctcctccaat | 1200 |
| ggcaaagtga | atggcaagcg | atcataccca | gagtctttct | ataagtcaac | acctctggtg | 1260 |
| cctgaagtgg | cccaggagat | tcctctgacc | ttgagtgtgg | atgacttcag | gcagcctcgg | 1320 |
| tacagcagca | atggtaacct | agagacacct | tctaaaaggg | ctcccacgaa | ggggaaagca | 1380 |
| ggaaagggca | agaggacgga | ccctgaccac | tatgaaacag | actacacgac | aggtggggag | 1440 |
| tcctgcgagg | agctggagga | ggactgggtc | agggaatatc | cacctatcac | ttcagatcaa | 1500 |
| caaagacaac | tctacaagag | aaattttgat | gcaggtctgc | aggagtataa | gagcttacag | 1560 |
| gcagaactag | acgacgtcaa | taagagctc | tctcgtctag | ataaagagct | ggatgactac | 1620 |
| agagaggaga | gtgaagagta | catggctgct | gctgatgaat | ataatagact | aaagcaagtt | 1680 |
| aagggatctg | cagattataa | aagtaagagg | aattactgca | agcagttgaa | gagcaaatta | 1740 |
| tcgcacatca | agaggatggt | gggagactat | gacagacgga | aaccttagag | agatgccagt | 1800 |
| tgcgggagaa | gggagaggtg | catctgcctg | cacgatgtct | ctgcaattct | ctccagaggc | 1860 |
| aaactgactt | tggactctaa | tctgggaagt | taaaactttg | tgatcattac | aaagtttcca | 1920 |
| tggctttaat | tccatcagtt | tcctatctcc | agtattgaag | cattttataa | atggcttttg | 1980 |
| ataattgact | gggctgaaca | ctccaattaa | ggattttaca | gtttcaacat | tgattcttgt | 2040 |
| attaagaatt | aaaatgttgc | ttgaggtttt | aaatgtcaag | aaaggtcctg | gtgtgagctg | 2100 |

-continued

```
tgatgtgtgt gagctgtgat gtgaaggttc acacgccagg cagcgtgttc ctccaggtag    2160
accgtctaat caatctttgc agcagccctc aggtgactgt tatttagaat caggttgttt    2220
ttggttttcc agacagggtt tctctgtgta gccctggctg acctagaact tacgctgtag    2280
accaggctgg ccttgaactc acacagctcc tctgagtgct ggtgcaggag ttaacgtcgt    2340
ggaccggtat catcactttt cctgcggtga cttctccaaa ctgaaactgc taaggcagtt    2400
ttggctaagt ctgttttatg actgcaaatg acagcattcc tgcctttgta tttcagggga    2460
aatacgatac attatatcgg ccatgttccc caccactgtt tttcttatat tgacttttaa    2520
caaatgaata ggattatttt tggctttaca ttttttccta acacttaaga tcatataaaa    2580
ttaacaaata tgtgaaattt aagaattgta aatatatatt tacgtttgaa agatgatttt    2640
aaatccaggg ttaaagtgct ttttatcttg tatagtttac atgctttttt ttttttttga    2700
taacccacta gacctttcca ttgtatcaga gtatccaatt acatttacaa ttatgacttg    2760
aattgtattt cacaggaatg ctcaagtttt gtacatattt tataaggtat taaacctgat    2820
gttctctttc taaaaaaaa                                                 2839
```

<210> SEQ ID NO 4
<211> LENGTH: 1920
<212> TYPE: DNA
<213> ORGANISM: Gallus gallus
<300> PUBLICATION INFORMATION:
<302> TITLE: Occludin: A novel integral membrane protein localizing at tight junctions
<303> JOURNAL: J. Cell Biol.
<304> VOLUME: 123
<305> ISSUE: 6
<306> PAGES: 1777-1788
<307> DATE: Dec 1993
<308> DATABASE ACCESSION NUMBER: D21837

<400> SEQUENCE: 4

```
caaagcggcg gagggccacc atgttcagca agaagtccta cgacggcccc ccgcgggggt    60
acggcccccc cacggggtac ggcgccccca cggctgatta cggctacggg tctccgccgc    120
cgggctccta ctacgtggac gacgctccgc agctcttcta caagtggacg tcgccgcccg    180
gcgcggtgcg gggctgcag gcggggtcc tcgtgctgtg catcgccatc ttcgcctgcg    240
tcgcttccac gctcgcctgg gattacggct acggcctggg ggggcgtac ggcaccgggc    300 tggggggtt ctacggctcc aactactacg gcagcgggct gagctacagc tacggctacg    360
ggggctacta cggagggtg aaccagcgca cggccaacgg cttcatgatc gccatggccg    420
tgctgtgctt cctggcccag ctgggcgctg tggtggcggc gctcagcaaa tccggggcca    480
cgcgctcgcg gcgcttctac ctggccgtgc tggtgctgag cgccgtgctg gccttcgtca    540
tgctcatcgc ctccatcgtc tacatcatgg gcgtcaaccc gcaggcgcag atgtccagcg    600
gttactacta cagccccttg ttggccatgt gcagccaggc ctacggcagc acctacctca    660
accagtacat ctaccactac tgcaccgtgg accccagga ggctgtggct gctgtctgtg    720
ggttcctcat cgtcatcctg ctctgcctca tctgcttctt cgcccagaag acgcgcagta    780
agatctggcg ctacggcaaa gccaacatct actgggaccg cgccgccgtg gtgcaggagg    840
ggcctgacgt ggaggagtgg gtgaagaacg tggcggatgg ggccagcgtg caggacgaga    900
cggccacgct tgcctactcg gagaagccca ccagccctgt cgccgccccc ccctacagct    960
acgtgccccc ccccagcgct gggtactacc cctcgggcac ctacagcagc cggggcgacc    1020
agccggaccg ggccctcagt gccagccctg tgcatgggga ggaggaggag gagaagggga    1080
```

```
aggatcagcc cagcagaccg cccgcccgcc ggggccgccg ccgccgccgt aaccccgagt    1140
tggatgagtc ccagtatgag accgactaca ccacggccgt ggagtccagt gatgagcggg    1200
accaggagca gtgggccagt ctgtacccccc ccatcacgtc ggacggcgcc cgccagcgct   1260
acaagcagga gttcgacacc gacctgaagc gctacaagca gctctgtgct gagatggaca    1320
gcatcaacga ccgcctcaat cagctcagcc gacggctcga cagcatcacc gaggacagcc    1380
ctcaatacca ggatgtggca gaggagtaca atcagctcaa agacctgaag cggagcccag    1440
actaccaaag caagaagcag gagagcaaag tgctgcgcaa caagctcttc cacatcaagc    1500
gcatggtgag cgcctacgac aaggtgcggg ggtaaccagc accagcagga gggggggggca   1560 ccccccacccc cccacccaaa gactgttgtg cattttgtac cttcttctta aaagaaaaaa   1620
cacactcaat cacatccacc ccccccccaa agggtcacc cccccaacc cccccttaac      1680 ccctcccact ccatccactg tgaatgcacc cactgagtgt tgggggctgc ccccccccc     1740 cgtgctgtta ttatggtagt ggggggggggg ggggagctgt gtaaggccca cacctctggg   1800
aagggctgag gtctgcaaca gcatcacagc cgccctggca ctgtgggtac cagaatggta    1860
ccctgagcac acagctcaag gtgggggggg gagcatccct tgggatgggg ggggggggca    1920

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Human
      occludin antisense oligonucleotide

<400> SEQUENCE: 5
aagaggcctg gatgaca                                                     17

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Human
      occludin scrambled oligonucleotide

<400> SEQUENCE: 6
gcaagtcagg acgtaga                                                     17
```